US009550031B2

(12) United States Patent
Van Sickle et al.

(10) Patent No.: US 9,550,031 B2
(45) Date of Patent: Jan. 24, 2017

(54) DEVICE AND METHOD TO MONITOR, TRACK, MAP, AND ANALYZE USAGE OF METERED-DOSE INHALERS IN REAL-TIME

(75) Inventors: John David Van Sickle, Oregon, WI (US); Gregory F. Tracy, Madison, WI (US)

(73) Assignee: Reciprocal Labs Corporation, Madison, WI (US)

( * ) Notice: Subject to any disclaimer, the term of this patent is extended or adjusted under 35 U.S.C. 154(b) by 921 days.

(21) Appl. No.: 12/348,424

(22) Filed: Jan. 5, 2009

(65) Prior Publication Data
US 2009/0194104 A1   Aug. 6, 2009

Related U.S. Application Data

(60) Provisional application No. 61/025,511, filed on Feb. 1, 2008.

(51) Int. Cl.
*A61M 15/00* (2006.01)

(52) U.S. Cl.
CPC ........... *A61M 15/00* (2013.01); *A61M 15/008* (2014.02); *A61M 2205/3306* (2013.01); *A61M 2205/3317* (2013.01); *A61M 2205/3553* (2013.01); *A61M 2205/3592* (2013.01); *A61M 2205/6027* (2013.01); *A61M 2205/6054* (2013.01); *A61M 2205/6063* (2013.01); *A61M 2209/01* (2013.01)

(58) Field of Classification Search
CPC ................ A61M 15/00; A61M 15/008; A61M 2205/6027; A61M 2205/3553; A61M 2205/3306; A61M 2206/3306; A61M 2206/3317; A61M 2206/3592
USPC ......................... 128/200.14–200.23, 204.18, 204.21,128/204.22, 205.23, 920, 925
See application file for complete search history.

(56) References Cited

U.S. PATENT DOCUMENTS

| 5,284,133 | A |   | 2/1994  | Burns et al. |
|---|---|---|---|---|
| 5,363,842 | A |   | 11/1994 | Mishelevich et al. |
| 5,477,849 | A |   | 12/1995 | Fry |
| 5,505,192 | A |   | 4/1996  | Samiotes et al. |
| 5,544,647 | A | * | 8/1996  | Jewett et al. ............ 128/200.23 |

(Continued)

OTHER PUBLICATIONS

International Search Report for Application No. PCT/US2010/20055 dated May 25, 2010 (2 pages).

(Continued)

*Primary Examiner* — Justine Yu
*Assistant Examiner* — Timothy Stanis
(74) *Attorney, Agent, or Firm* — Fenwick & West LLP

(57) ABSTRACT

A system and method for accurately and reliably determining and recording the time, date and location where a medication is used, and a system and method for transmitting, collecting, and using that data to improve clinical care, disease management, and public health surveillance. The device allows information concerning drug usage, including the time, date and location of use, to be transmitted to a remote network computer system so that the data can be evaluated to determine current impairment and future risk, and to identify changes in the frequency, timing, or location of medication usage indicative of change in disease control or management, and to examine spatial, temporal or demographic patterns of medication use or absence of use among individuals and groups. In addition, the device may further be configured to transmit signals indicative of its status, condition or other results to the remote network computer system.

26 Claims, 7 Drawing Sheets

(56) References Cited

U.S. PATENT DOCUMENTS

| | | | |
|---|---|---|---|
| 5,622,163 A * | 4/1997 | Jewett et al. | 128/200.23 |
| 5,809,997 A | 9/1998 | Wolf | |
| 5,976,082 A * | 11/1999 | Wong et al. | 600/300 |
| 6,076,521 A | 6/2000 | Lindahl et al. | |
| 6,190,326 B1 * | 2/2001 | McKinnon et al. | 600/529 |
| 6,202,642 B1 | 3/2001 | McKinnon et al. | |
| 6,540,672 B1 | 4/2003 | Simonsen et al. | |
| 6,579,231 B1 * | 6/2003 | Phipps | 600/300 |
| 6,637,430 B1 | 10/2003 | Voges et al. | |
| 6,652,455 B1 * | 11/2003 | Kocher | 600/300 |
| 6,729,327 B2 | 5/2004 | McFarland | |
| 6,743,202 B2 * | 6/2004 | Hirschman et al. | 604/131 |
| 6,747,556 B2 | 6/2004 | Medema et al. | |
| 6,804,558 B2 * | 10/2004 | Haller et al. | 607/30 |
| 6,937,150 B2 | 8/2005 | Medema et al. | |
| 6,958,691 B1 | 10/2005 | Anderson et al. | |
| 7,151,456 B2 | 12/2006 | Godfrey | |
| 7,191,777 B2 | 3/2007 | Brand et al. | |
| 7,481,213 B2 | 1/2009 | Childers | |
| 7,537,005 B2 | 5/2009 | Dave | |
| 7,766,012 B2 | 8/2010 | Scheuch et al. | |
| 2002/0073196 A1 | 6/2002 | Westervelt | |
| 2003/0098022 A1 * | 5/2003 | Nakao et al. | 128/200.21 |
| 2003/0221687 A1 * | 12/2003 | Kaigler | A61M 15/00 128/200.14 |
| 2004/0148199 A1 | 7/2004 | Dixon | |
| 2004/0199056 A1 * | 10/2004 | Husemann et al. | 600/300 |
| 2005/0021286 A1 * | 1/2005 | Kunce | 702/179 |
| 2005/0028815 A1 | 2/2005 | Deaton et al. | |
| 2005/0086256 A1 * | 4/2005 | Owens | 707/103 R |
| 2005/0150488 A1 * | 7/2005 | Dave | 128/200.14 |
| 2005/0172958 A1 | 8/2005 | Singer et al. | |
| 2005/0247312 A1 | 11/2005 | Davies | |
| 2006/0089545 A1 | 4/2006 | Ratjen et al. | |
| 2006/0231109 A1 | 10/2006 | Howell et al. | |
| 2006/0237001 A1 | 10/2006 | Stangl | |
| 2006/0237002 A1 * | 10/2006 | Bonney et al. | 128/200.23 |
| 2007/0023034 A1 | 2/2007 | Jongejan et al. | |
| 2007/0186923 A1 | 8/2007 | Poutiatine et al. | |
| 2007/0271298 A1 | 11/2007 | Juang et al. | |
| 2008/0125724 A1 * | 5/2008 | Monroe | 604/264 |
| 2008/0201169 A1 | 8/2008 | Galasso et al. | |
| 2008/0281636 A1 | 11/2008 | Jung et al. | |
| 2009/0128330 A1 | 5/2009 | Monroe | |
| 2009/0326861 A1 | 12/2009 | Langford et al. | |
| 2010/0192948 A1 | 8/2010 | Sutherland et al. | |
| 2010/0252036 A1 | 10/2010 | Sutherland et al. | |
| 2011/0253139 A1 | 10/2011 | Guthrie et al. | |
| 2011/0290256 A1 | 12/2011 | Sather et al. | |

OTHER PUBLICATIONS

National Heart, Lung, and Blood Institute. Expert Panel Report 3: Guidelines for the Diagnosis and Management of Asthma FullReport 2007. United States.

Centers for Disease Control and Prevention. Surveillance for Asthma—United States, 1980-2004. Morbidity and Mortatlity Weekly Report (MMWR). Oct. 19, 2007; 56(SS-8):1-60.

Bateman ED, et al. Can guideline-defined asthma control be achieved? The Gaining Optimal Asthma ControL study. Am J Respir Crit Care Med. Oct. 15, 2004;170(8):836-44. US.

Nathan RA, et al. Development of the asthma control test: a survey for assessing asthma control. J Allergy Clin Immunol. Jan. 2004;113(1):59-65. United States.

Frey, Complexity of chronic asthma and chronic obstructive pulmonary disease: implications for risk assessment, and disease progression and control. Lancet. 2008;372(9643).

PCT International Search Report and Written Opinion, PCT Application No. PCT/US14/39014, Oct. 23, 2014, 16 pages.

* cited by examiner

DEVICE AND METHOD TO MONITOR, TRACK, MAP, AND ANALYZE USAGE OF METERED-DOSE INHALERS IN REAL-TIME

CROSS REFERENCE TO RELATED APPLICATIONS

This application claims priority from U.S. Provisional Patent Application Ser. No. 61/025,511, entitled "A device and method to monitor, track, map, and analyze usage of metered-dose inhalers in real-time", filed on 1 Feb. 2008. The benefit under 35 USC §119(e) of the United States provisional application is hereby claimed, and the aforementioned application is hereby incorporated herein by reference.

FEDERALLY SPONSORED RESEARCH

Not Applicable

SEQUENCE LISTING OR PROGRAM

Not Applicable

TECHNICAL FIELD OF THE INVENTION

The present invention relates generally to inhalers. More specifically, the present invention relates to a device and method for tracking and analyzing the location, timing and frequency of usage of medication inhalers, such as those used to treat asthma, chronic obstructive pulmonary disease, and other medical conditions.

BACKGROUND OF THE INVENTION

Asthma remains a significant and costly public health problem. In the United States, more than 22 million people have the disease; worldwide, the World Health Organization estimates the population with asthma may be 300 million, and predicts that it will rise to 400 million by 2025.

Despite the development of new medications, rates of hospitalizations and emergency room visits have not declined. Each year in the United States the disease causes approximately 2 million emergency department visits, 500,000 hospitalizations, and 5,000 deaths. In addition, asthma is responsible for an estimated 15 million missed days of school, and 12 million days of work. Total annual costs to US health insurers and employers are greater than $18 billion.

The majority of these exacerbations could be prevented with currently available treatments, however, only 1 in 5 asthmatics has the disease under control. Newly revised national guidelines urge doctors to more closely monitor whether treatment is controlling everyday symptoms and improving quality of life. Physicians, however, have few available tools to assess how well their patients are doing day-to-day. An increasing number of physicians have begun to use periodic, written questionnaires (such as the Asthma Control Test) to monitor patients and determine their level of control. These instruments require patients to accurately recall and report the frequency of symptoms, inhaler usage, and activity level and restriction over some period of time (usually two to four weeks). As a result, these questionnaires are subject to error introduced by biases (recall), different interpretations of symptoms, and behaviors (non-adherence), and only provide information at the time they are used.

Nearly all persons with asthma carry an inhaled medication to immediately relieve symptoms wherever they occur. The frequency with which patients use these medications is one of the most important indicators of how well their disease is controlled. Physicians who could remotely monitor the use of these medications by patients in real-time would be able to identify and help patients in need of additional attention before they suffer an exacerbation.

Asthma is unique in that important medication(s) are often used at the location and time of exposures that cause exacerbations. Many exacerbations are caused by exposure to environmental factors such as allergens, air pollutants, tobacco smoke, and occupational chemicals, but identifying causative exposures or locations that pose a particular threat has been a struggle for public health experts.

Since established risk factors do not explain the prevalence of asthma or its trends over time, it is likely that there are unknown environmental factors that trigger symptoms or contribute to the development of asthma.

Public health officials have been limited to the retrospective analysis of the small proportion of attacks that led to emergency room visits and hospitalizations (the most severe exacerbations). These events indicate where the patient lives or the location of the health facility where they received treatment, but provide no information about where their exacerbation began. Last year, the US Centers for Disease Control and Prevention recommended that the timeliness and geographic specificity of asthma surveillance data be improved.

As a result, real-time tracking and mapping of the locations where persons with asthma use their inhaled medications would improve scientific assessment and management of asthma, and enable better public health surveillance of asthma and its relationship to environmental exposures. Studies of epidemic asthma have demonstrated that understanding the locations where asthma exacerbations occur can help identify important new exposures.

In addition, many patients with asthma triggered by exposures at school or work do not recognize the relationship between their symptoms and specific locations, resulting in missed opportunities to avoid or mitigate the exposure and thereby prevent further exacerbations.

At present, there are no commercially available devices that allow the location where an inhaler is used to be objectively obtained. In addition, there are no commercially available devices that allow physicians to monitor the medication use of their patients in real time, to gauge their control over the disease, and to use technology to determine who needs additional attention. Furthermore, there are no systems that allow public health officials to collect and analyze data on the medication use of individual patients in order to monitor in real time the overall burden of the disease in the community or to guide public health interventions and epidemiological research.

Various systems have been proposed to record the time and date of usage of metered dose inhalers. Two models are currently available in the U.S. market. One device, described in U.S. Pat. No. 5,505,192, attaches to the end of a metered dose inhaler and records the time and date of inhaler use over a 30 day time period. Another device, described in U.S. Pat. No. 6,202,642, captures the time and date of inhaler use, and provides a means to transmit this information at a later time to the health care provider. To accomplish this, the patient must connect their device to a computer.

Several devices that provide means for the two-way transmission of information between a medication and a remote network using wireless technologies have also been proposed. U.S. Pat. No. 6,958,691 describes an inhaler having an electronic data management and display system and a communicator for wireless communication with a network computer system. US application 2006/0089545 proposes use of a cellular phone to transmit information about medication, and to present medication information and treatment instructions to the patient.

The primary aim of both of these devices is to encourage and improve patient compliance with their prescribed medication regimen. As a result, these systems focus on providing education (treatment instructions), monitoring, and supervision. In addition, the above devices provide for two-way communication between the inhaler (or device) and the physician or health care provider, and some allow for controlling or modifying the medication delivered by the inhaler (see U.S. Pat. No. 5,477,849).

Various methods for the epidemiological analysis of medical data and information (such as emergency room visits or hospitalizations, or over the counter medication purchases) have been proposed. However, these systems are focused on establishing a diagnosis or on tracking and analyzing the geographic location(s) of health care utilization (such as emergency room visits or hospitalizations) or the residence of the person with the disease of interest. No known system describes the analysis of the location where the medication is used, or proposes a system for aggregating and making use of information from a population of individuals.

SUMMARY OF THE INVENTION

The present invention comprises a device that, when attached to a metered dose inhaler, or other medication or medical device, determines the location, time, and date when the medication or medical device is used, and communicates that information to a remote network computer system. The device includes supporting electronics (microprocessor, memory, etc.), an electronic data management system, a use sensor, a communication device, antenna(s), and a battery. The device is capable of wireless communication with a network computer system to enable communication of data between the electronic data management system and the network computer system.

In a first embodiment, the device uses a terminal device, such as a cellular phone, and the in-built capabilities of the terminal device and/or its associated network, to determine its location and to transmit information about the time and location the medication is used to the network computer system.

In another embodiment, the device utilizes an autonomous global positioning system receiver and a communication device to wirelessly communicate the geographic position and time and date of use directly to a network computer system.

In either embodiment, the present invention comprises a collection of software applications running on the network computer system that receive, analyze, and display the collected data in online interfaces, and provide means for a wide variety of operations.

For example, used together, the system, the device, and the online interfaces generate real-time displays and maps of asthma medication use; collect and deliver information on the use of inhaled medications to inform and guide management of the disease; perform statistical analyses to identify spatiotemporal clusters and temporal aberrations; and deliver alerts to authorized users, such as the patient and the patient's health care providers.

By providing information about the timing and frequency of use of the medication or medical device, and identifying the geographic location where an individual uses their medication or medical device, the system may facilitate better management of a variety of diseases by the patient and their health care provider, and improve recognition of specific locations (such as workplace, school, or home, among others) that precipitate exacerbations in order that the patient may avoid or modify these locations to prevent future exacerbations.

By aggregating and analyzing the aggregated information about the temporal patterns and geographic locations of individual patterns of medication use, the device and method provide public health and environmental health agencies with a real-time means to (A) identify clusters of exacerbations, (B) assess the burden of disease in a population or some portion of the population, and in some geographic area, (C) plan and evaluate public health interventions to reduce morbidity, and (D) detect new epidemiological patterns or risk factors.

The invention includes both the monitoring system and the methods by which the device and system are utilized by patients, health care providers, scientists and researchers, and public and environmental health agencies, among others.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DETAILED DESCRIPTION OF THE INVENTION

In the following detailed description of the invention and of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, mechanical, electrical, and other changes may be made without departing from the scope of the present invention. The following detailed description is, therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention.

Referring to the Figures, it is possible to see the various major elements constituting the apparatus of the present invention. The present invention provides a system and method for reliably determining and recording the time, date, and location where a metered dose inhaler is used and a system and method for transmitting, collecting, and using that data to improve clinical care, disease management, and public health surveillance.

Figure 1:
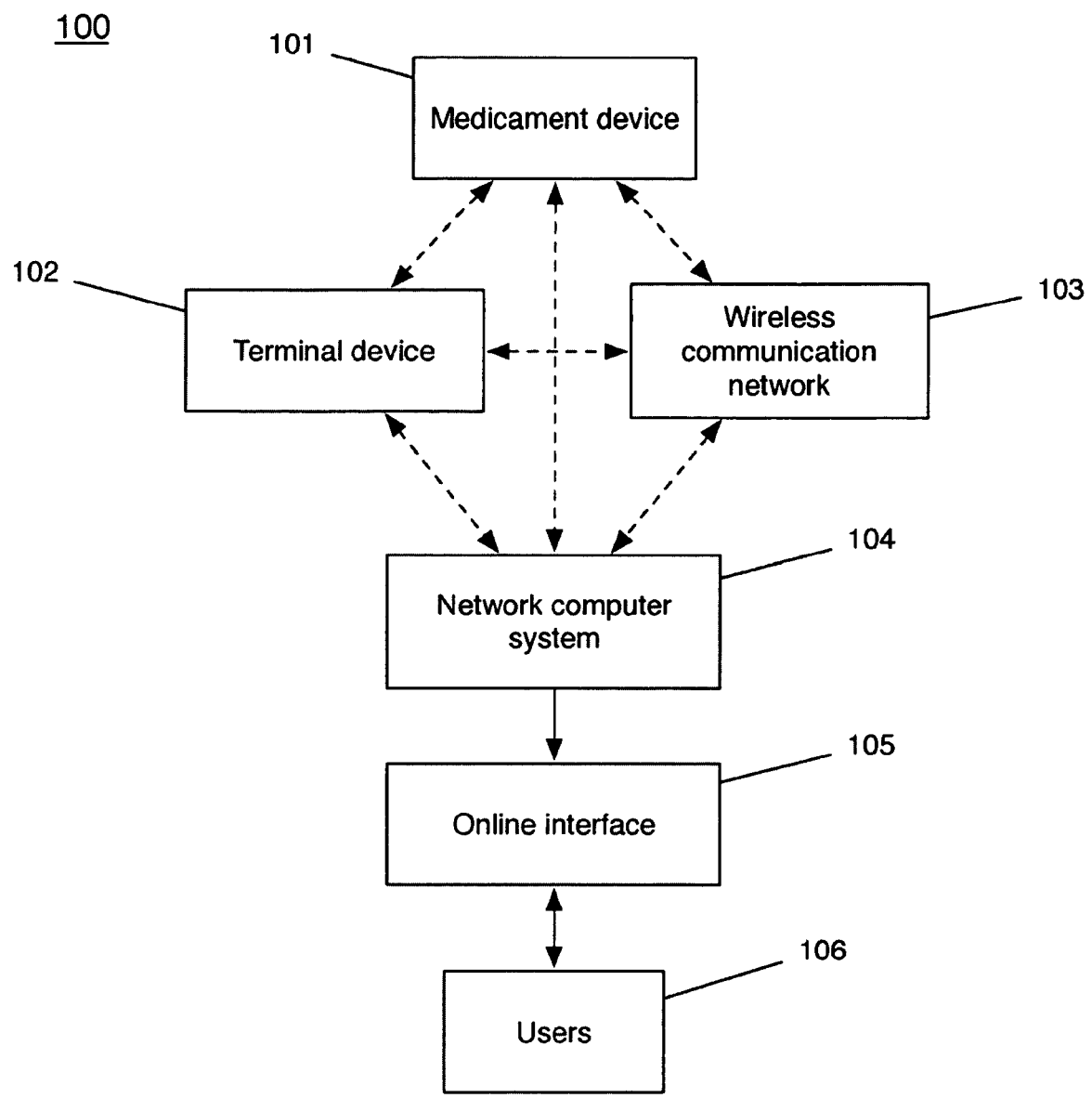
FIG. 1 is a schematic outlining a complete system for monitoring medication use by a patient.

FIG. 1 illustrates the overall flow of information 100 from a medicament device 101 attached to an inhaler, to the terminal device 102 (if used), to a wireless communication network 103 (if used), to a remote network computer system or server 104, and finally an online interface 105 for use by one or more users 106.

FIGS. 2a, 2b, 2c and 2d show schematic diagrams of the first and alternative embodiments of the medicament device shown in FIG. 1 that are suitable for use in a system according to the present invention. The device is attached to the medicament dispenser or housing 207, and contains a medication canister 201, a cap or collar or tag or label 202, a communication device 203, supporting electronics 204, a power supply 205, an actuation detector 206, and in an alternative embodiment, a global positioning system receiver 208.

The medicament device is mechanically coupled to the medicament dispenser 207 containing the medication canister 201 and suitably attached to the medication canister 201 by any suitable mechanical mechanism including grip mechanisms, snap-fit mechanisms, strap(s), clamp(s), and adhesive fixing. The unit may, for example, form a snap-fit module that is received or is receivable by the medicament housing 207 shown in FIG. 2a, or may be mounted on the top of the medication canister 201 by mechanical means shown in FIG. 2b. In either embodiment, the medicament device is simple to install, attaches securely, is easily removed and transferable to replacement medicament dispensers, fits numerous dispensers, and is compatible with all applications. In aspects, the medicament device or any distinct device aspects of the system may be adapted to be worn on the body of the user. Examples would include belt-attachable devices, and devices in the form of watches for wrist or leg attachment.

The system additionally comprises a detector for detecting dispensing from the medicament container, or a means for obtaining information related to the dispensing of the medication. The means may be a use sensor or a detector for detecting movements, for example, the activation of the dispensing mechanism. The use sensor is essentially a switch, the main characteristic of which is that it should close an electrical circuit when the drug is delivered and, as a result, send a signal to the microprocessor of the device. The dispenser monitoring system is operationally transparent to the user in that it monitors each dose automatically upon actuation of the dispenser without any additional action on the part of the user.

In the first embodiment, the sensing is achieved by an actuation detector 206 including an miniature magnet and a magnetic field sensor. The miniature magnet of the actuation detector 206 is integrated into a cap or collar 202, which is mounted to the top of the medication canister 201. A magnetic field sensor of the actuation detector 206 is then housed within or on the stationary body of the medicament device. When the user actuates the inhaler canister, the canister is depressed, and the magnet is carried toward the magnetic sensor. When the magnet is brought in proximity to the magnetic sensor, the sensor acts as a magnetically actuated switch causing a voltage output change in the sensor, which is recorded. In one embodiment, a bounce filter circuit element, composed of, for example, a charge capacitor and a threshold detector, is installed in order to eliminate the possible effect of extra bounce pulses resulting from bouncing or vibration of the canister.

Other suitable techniques for the actuation sensor switch include detectors using detection of capacitive or thermodynamic effects, optical detectors, or mechanical levers, among others.

Figure 2A:
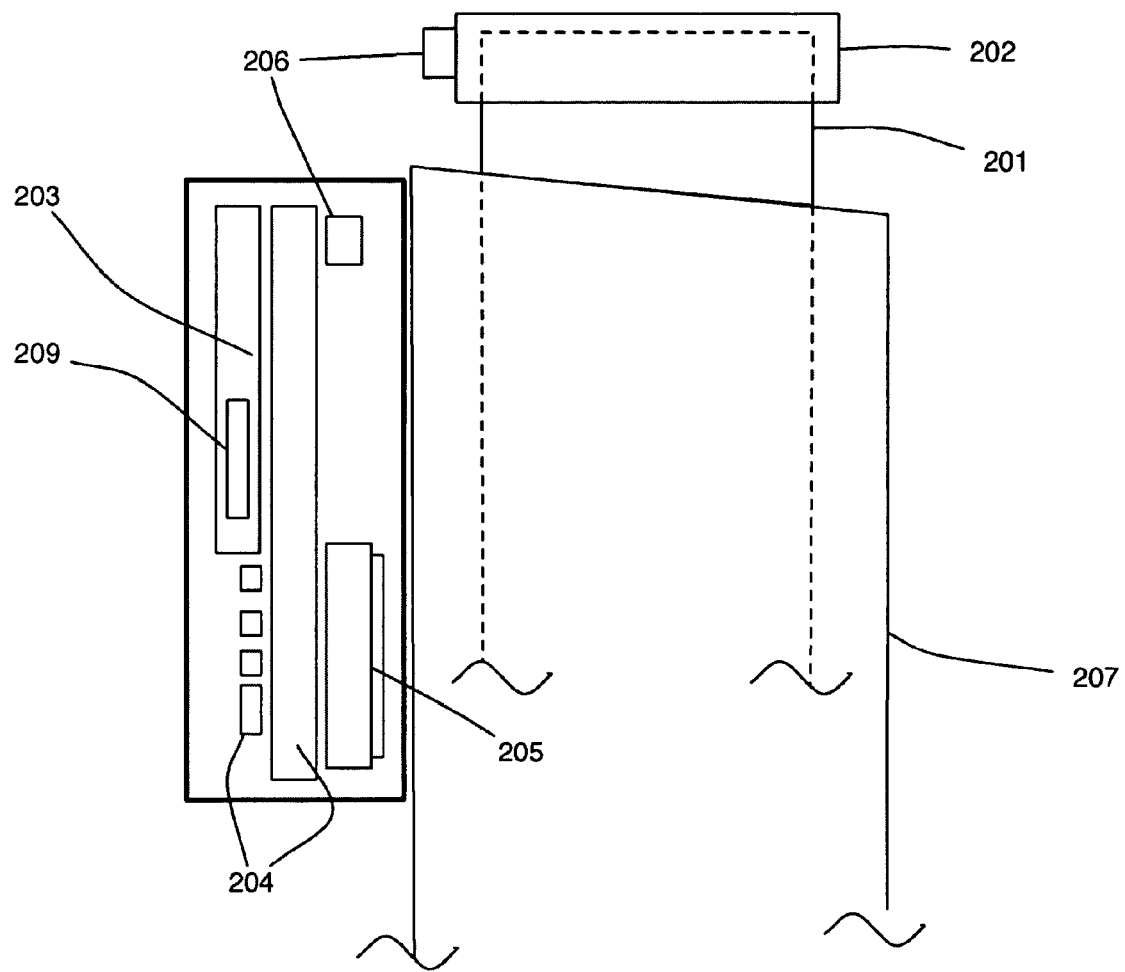
FIGS. 2a, 2b, 2c, and 2d are schematic diagrams of the medicament device in the first and alternative embodiments.
Figure 2B:
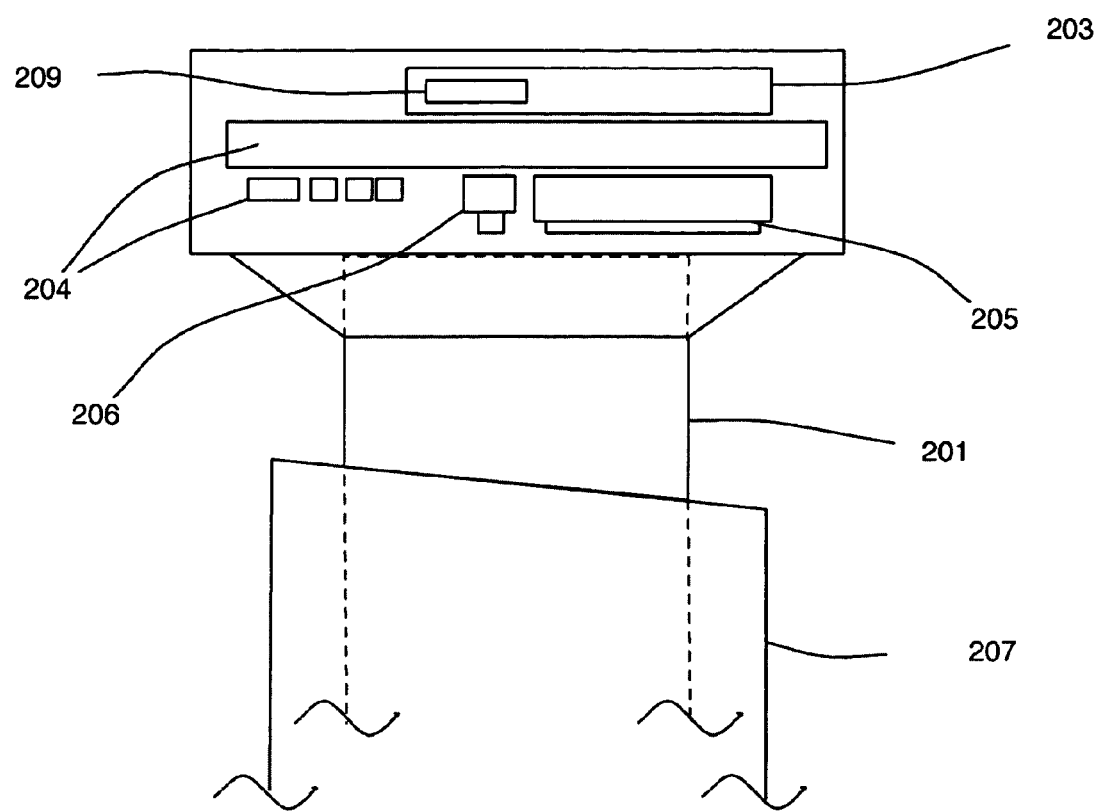

For example, in another embodiment shown in FIG. 2b, the device is entirely contained in a package mounted on the end of the medication canister 201. A mechanical switch 216 integrated into the package, consisting of, for example, a spring-loaded lever, force sensing resistor or contact rod, monitors the dispensing of the medication and is mechanically depressed or electrically actuated in response to the downward movement of the medication canister 201.

Figure 2C:
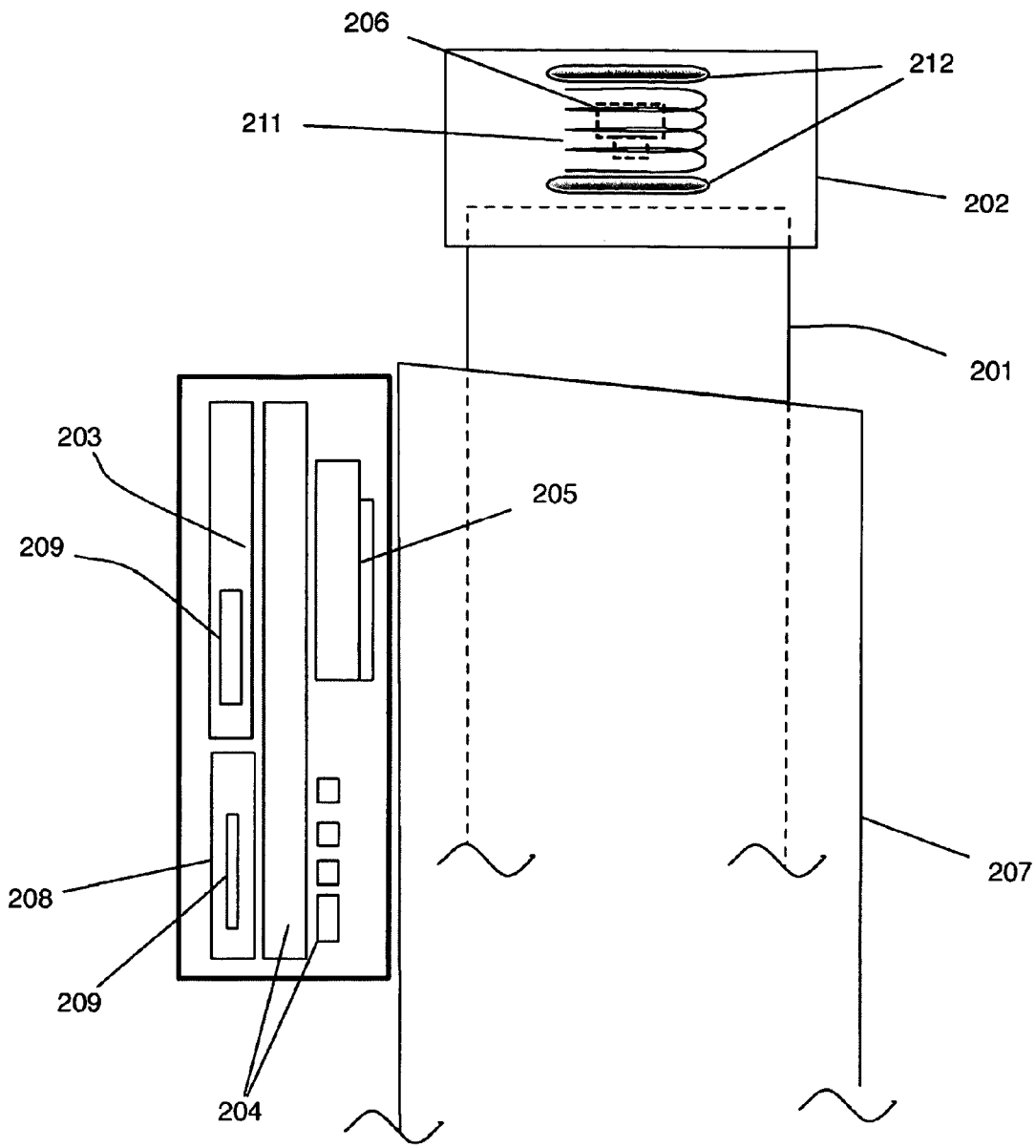

In another embodiment shown in FIG. 2c, similar switch mechanisms are integrated into a cap mounted onto the medication container 201 and connected by leads to the medicament device, which is attached to the side of the medication housing 207. The actuation detector 206 includes a momentary push button switch surrounded by a spring 211 and discs 212. When the user actuates the inhaler canister, the cap and canister are depressed, compressing the discs and spring and closing the switch circuit signaling actuation of the inhaler. The tension of the spring 211 is set to preclude accidental actuation of the switch circuit, when no actuation of the inhaler occurs or is intended.

Figure 2D:
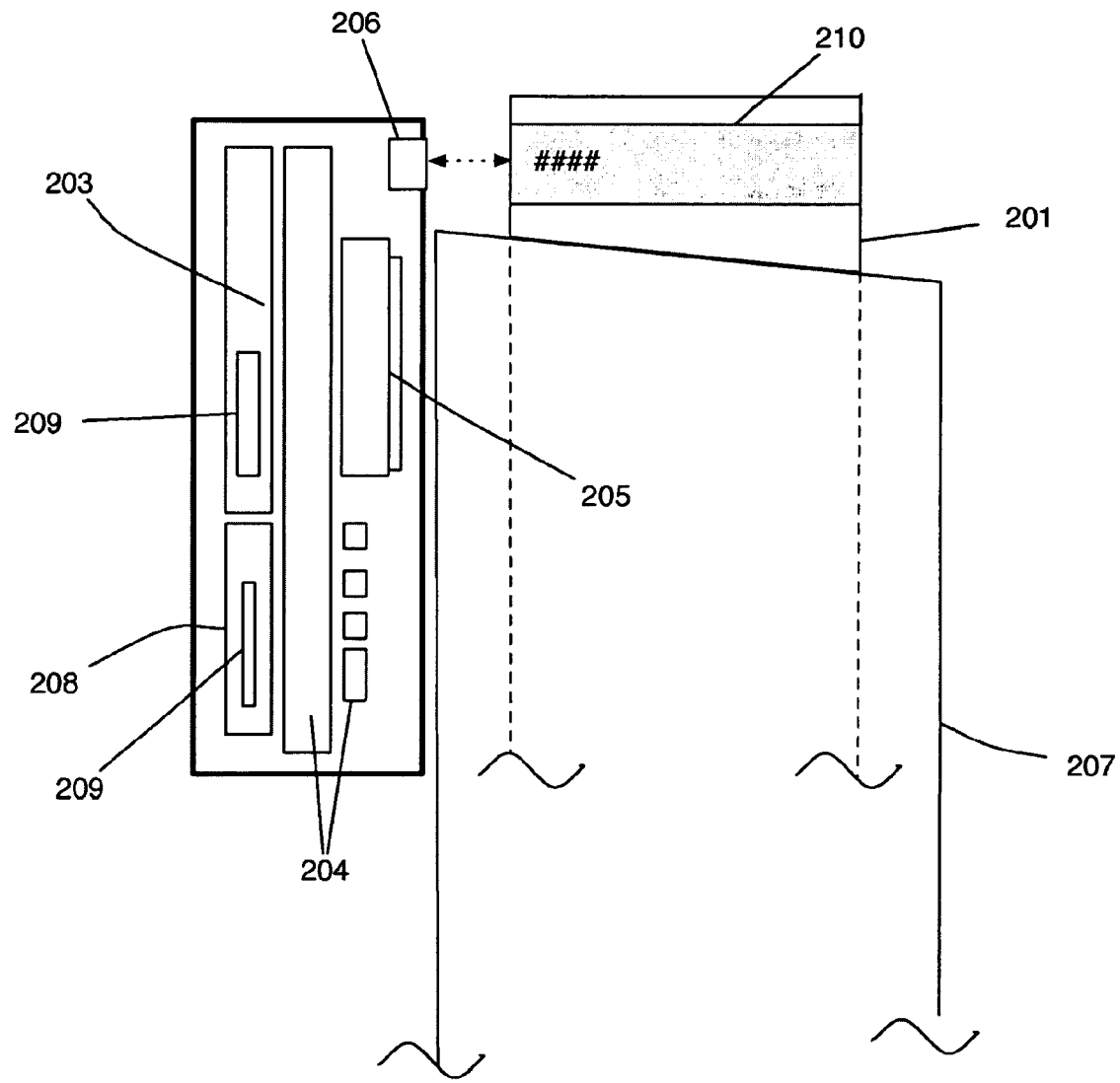

In another embodiment shown in FIG. 2d, a small tag or label 210 containing a pattern is attached or fixed atop the medication canister 201, by any suitable means including adhesive fixing, grip mechanism, snap-fit arrangements or through the use of various mounting means. The mounting means may, for example, comprise an adhesive label, wrap-around tape, or cap or collar arrangements. The actuation detector 206 includes an optical sensor on the medicament device that monitors the tag or label on the canister. Each time the medication canister 201 is depressed, the optical sensor image of the pattern is disrupted, and actuation of the inhalation device is signaled to the controller.

In another embodiment, the switch is integrated into the medicament device itself, with a contact lever extending out the back of the device packaging into the area above the top of the medicament dispenser or housing 207. When the medication canister 201 is depressed, a cap 202 mounted to the top of the medication canister 201 contacts the switch and an actuation is detected.

In another embodiment, electrical contacts integrated into a cap 202 mounted on the end of the medication canister 201 meet corresponding electrical contacts on the device when the canister is depressed, closing a circuit.

In another embodiment, a lever or other element extends into the housing, and is positioned for movement each time the medication canister 201 is pushed downwards. Movement of the lever actuates a micro-switch on the controller indicating that the inhaler has been actuated.

In another embodiment, a mechanical switch is integrated into a cap or collar 202 that is mounted onto the top of the medication canister 201. The switch consists of a spring-loaded lever that is mechanically depressed by the body of the medicament device, the medicament dispenser or housing 207, or a collar around the housing by the downward movement of the canister 201 when it is actuated.

In another embodiment, a thermistor or similar sensor is used to measure the change in the temperature of the pressurized medication canister 201 resulting from the expulsion of medication and propellant. In the case of a thermistor, a typical circuit puts a constant current through the thermistor and measures the variation in voltage resulting from any change in the temperature of the medication canister 201. Each time the inhaler is actuated, the temperature of the canister 201 is temporarily decreased relative to its temperature prior to usage; this change is detected by the thermistor and the actuation of the inhaler is signaled to the controller 204.

Furthermore, the support electronics 204 arranged on the medicament device comprise a microprocessor and memory for storage of information related to the medication events. The memory comprises a non-volatile memory chip that is capable of storing the information, for example, when the transfer of data from the medicament device and the terminal device is disturbed, or during a predetermined period of time.

Preferably, the memory includes random-access memory such as a DRAM (dynamic random access memory) or SRAM (static random access memory), and nonvolatile memory such as an EEPROM (electrically erasable programmable read-only memory). The EEPROM can be used to store software programs executed by the microprocessor, such as software that controls the operation of the medicament device. In addition, the EEPROM allows the stored software programs to be remotely updated.

The medicament device is also provided with a power source 205 so as to power the electrical components. A suitable power source 205 is a battery, clockwork energy store, solar cell, fuel cell or kinetics-driven cell. The power source 205 may be arranged to be rechargeable or re-loadable.

In addition, the medicament device support electronics 204 may be fitted with light elements, for example, one or more diodes, or speakers. The medicament device can thereby provide a visual or audible indication when the battery capacity has reached a certain predetermined capacity level and/or provide a warning that it needs to be recharged. Other diode(s) can be arranged to provide a visual indication that an actuation has occurred, and that the message from the medicament device to a terminal device, the wireless communication network, or the network computer system, has or has not been transferred successfully.

Moreover, a communication device 203 for wireless communication with a terminal device 102, such as a cellular phone, a wireless communication network 103, and/or a network computer system 104, to enable transfer of data to and from the medicament device is arranged in the medicament device. The communication device 203 includes, inter alia, a transceiver and an antenna 209, and an embedded network server, or equivalent for transmitting or receiving data or the outcome of an operation on the data.

Moreover, the communication device 203 may be arranged for two-way transfer of information. Accordingly, a terminal device 102 or the wireless communication network 103 or the network computer system 104 can, in addition to receiving information from the communication device 203, transfer information to the communication device 203, for example, a packet to acknowledge receipt upon a successful transfer of information from the medicament device.

The so-enabled device may also have the capability to form local area networks with other similarly enabled devices to enable local transfer of data there between.

In one embodiment, the communication device 203 communicates with a terminal device 102 using radio frequency signals, for example, spread-spectrum radio frequency signals. A suitable spread-spectrum protocol is the BLUETOOTH standard that employs rapid (e.g. 1600 times a second) hopping between plural frequencies (e.g. 79 different frequencies). The protocol may further employ multiple sending of data bits (e.g. sending in triplicate) to reduce the effect of interference. Of course, the communication device 203 can use other means to communicate with a terminal device 102, for example, optical signals.

Figure 3:
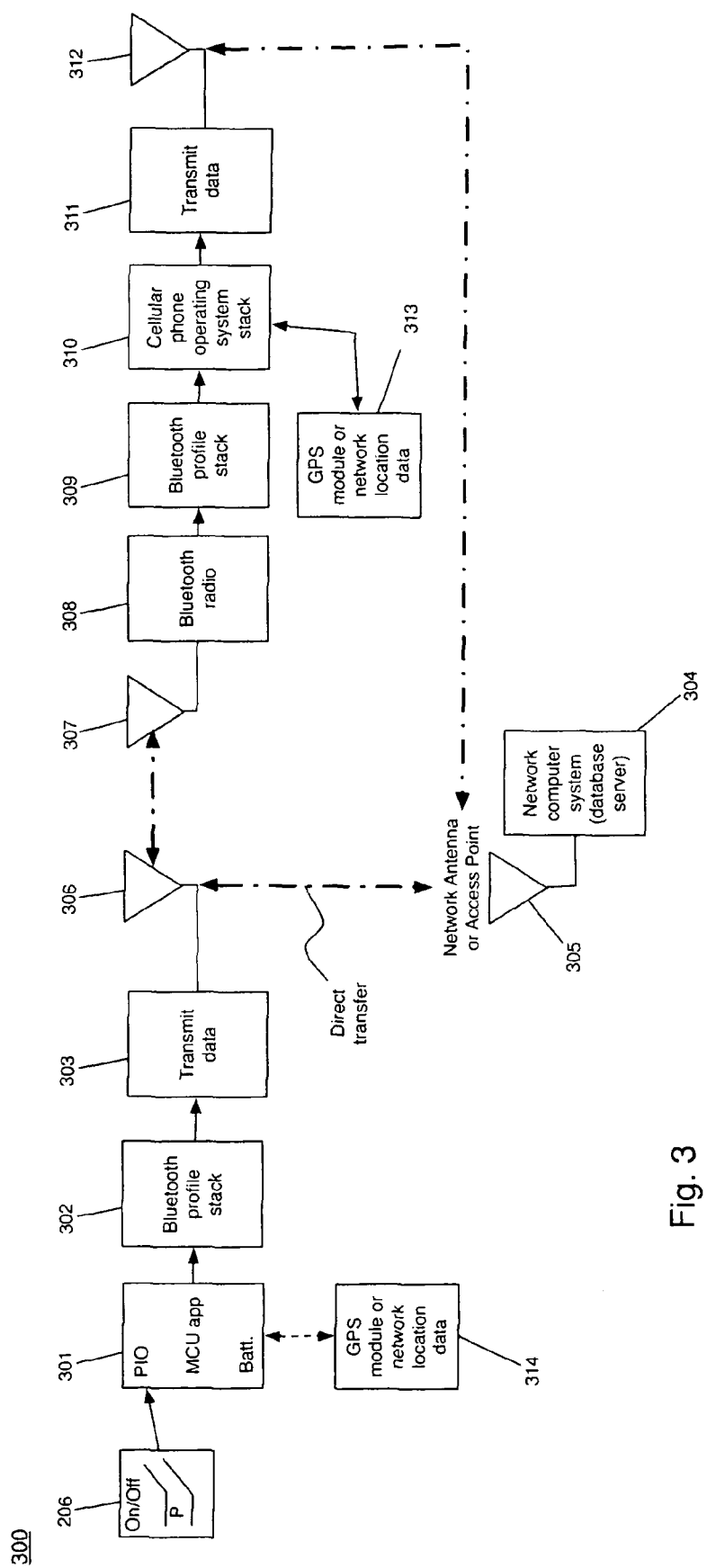
FIG. 3 is a schematic diagram illustrating the flow of information on the medicament device and the terminal device (if used) in the first and alternative embodiments.

In another embodiment, the medicament device 101 uses the communication device 203 to directly access a wireless communication network or a private or public network computer system as shown in FIG. 3, including one or ones that may also form part of a telecommunications system, which may itself be either a traditional copper wire system, a cellular system or an optical or microwave network, wireless metropolitan area networks (WMAN), broadband fixed access (BWA), wireless networks, such as wireless application protocol (WAP), 802.11 wireless LAN (WLAN), long-range RF networks, satellite networks, and distributed sensor networks (including stationary and dynamic), among others. Other suitable wireless communication mediums/methods include wireless digital data networks, two-way paging networks, specialized mobile radio systems, infrared, and non-licensed ISM-service communication links, such as the BLUETOOTH protocol. Further communication methods include Internet protocol (IP) addressing, among many others.

As a result, the communication device 203 may comprise an embedded network server to enable it to communicate directly with a network system, typically using Internet Protocol. The embedded network server will have hardware and software components and for example comprise an HTTP (web) server, an FTP (file) server or an SMTP (main) server. The embedded network server will typically be provided with a unique network address including an IP address, a website address, an e-mail address, or a file transfer protocol address.

The Internet is one suitable example of a public access network computer system, wherein the point of access thereto can be any suitable entry-point including an entry-point managed by an internet service provider. The public access network may also form part of a telecommunications system, which may itself be either a cellular system or an optical network or some other radio frequency signal network. In this embodiment, the network computer system comprises a public access network computer server system and a private access network system comprising for example, an Intranet or Ethernet which may, for example, be maintained by an individual, a municipality, a commercial entity, a healthcare provider, a service provider, a pharmacy, or a university medical center. Accordingly, the medicament device can communicate with one or more third parties, such as medical centers, healthcare providers, and other suppliers of healthcare products and services directly via the wireless communication system and the network computer system.

The medicament device 101 may therefore transmit and/or receive information to and from the network computer system 104 by means of a terminal device 102, a wireless communication network 103, and to the network computer system 104 directly, and between any and all of these means in any sequence.

The medicament device is configured to transmit various information over the network, such as the location, time, and date of medication events, the status or condition of the medical device (battery level, etc.) or the medication, self-test results, or even physiological data of a patient being treated with the medicament device.

This feature allows a remote operator to not only identify the time and location of the medicament device when it is used, but also to monitor the medicament device itself or events occurring in association with the medicament device at the remote site.

Of course, there are other conceivable types of medications and medical devices that are suitable for use in the system according to the present invention such as dry powder inhalers, and portable or stationary nebulizers, peak flow meters or spirometers, injectors, tablet dispensers, and medical devices such as blood pressure monitors, blood glucose monitors, canes, walkers, and pedometers.

In addition, examples of conditions that would be suitable for monitoring include asthma or chronic obstructive pulmonary disease, cystic fibrosis, non-cystic fibrosis bronchiectasis, forms of interstitial lung disease, reactive airways disease, occupational lung disease, and patients having fluctuations in congestive heart failure control. Because of the frequency of lung involvement, these devices will also be useful in the treatment and monitoring of patients after lung (or other solid organ) transplant or bone marrow transplant.

Referring now to FIG. 3, a block diagram of the flow of medication event information through the system 300. After the actuation detector 206 observes a medication event, an application is run by the microcontroller unit (MCU 301) which obtains information related to the medication. To this end, the means for obtaining information constantly monitors the dispensing of medication in order to register events, or the absence of events, related to the dispensing of the medication. A medication event may be, for example, that the patient using the medicament device dispenses the medication or fails to dispense the medication.

The information related to the medication event or events can be stored in the memory (as described above) of the medicament device or transferred to the network computer system either directly, or via a wireless communication network, or via a terminal device.

The information is then processed by a BLUETOOTH profile stack 302 and transferred to the communication device 303. Then the information is wirelessly transferred or sent via a wireless antenna 306 to the wireless antenna of a terminal device 307 or directly to the network computer system 304 through a wireless network antenna or access point 305.

In case of disturbances or the like of the information transfer, or if a link could not be established between the communication device 303 and the terminal device or the network computer system 304, preventing the communication device 303 from transferring the information to the network computer system 304 or the wireless receiving antenna of the terminal device 307 by a wireless antenna 306, the information may be stored in the memory of the medicament device, as mentioned above.

Thereafter, when a connection is established, the information can be sent or transferred to the terminal device or the network computer system 304.

When the terminal device receives the information through a BLUETOOTH radio 308, an acknowledgment receipt is transmitted back to the medicament device. Preferably, the user is notified by means including light (diode) means on the medicament device, as mentioned above. Other means may include audible signals, visualizing means, or vibration means. At this step, the medicament device performs any final processing and returns itself to its idle state, in order to minimize power consumption.

In the first embodiment, the terminal device is a cellular phone. Of course, there are other types of terminal devices that are suitable for use in the system according to the present invention, that have a communicator means and provide means to connect to and transmit data to a network computer system, including but not limited to pagers, modems, computers, portable music players, wristwatches, automobiles and vehicles, global positioning receivers and personal navigators, electronic medical devices, or other portable electronic devices.

In one embodiment, the terminal device contains a global positioning system (GPS) receiver and processor, which relies on the use of multiple communications signals and a triangulation algorithm.

An application on the terminal device monitors a communication port to determine when a message was received from the communication device 303 in the medicament device and processed by the BLUETOOTH profile stack 309. Upon receiving the message, the terminal device application generates a time stamp and processes the information by the operating system stack of the cellular phone 310 and a software application running on the cellular phone. The processing means of the terminal device determines the location of the terminal device at the time of receipt of the medication event information using the available means. Preferably, the geographic coordinates can be calculated locally from a global positioning system receiver and processor 313 in the terminal device. In that case, the terminal device application retrieves the necessary information and processes it.

Alternatively, the determination of location information may be accomplished using network-based technologies or solutions, wherein the location of the medicament device and/or the terminal device is identified based on a communication link connecting the medicament device and/or the terminal device with a remote locating service over the network. For example, certain cellular phone systems track the strength, the angle, and the arrival time difference of transmission signals for determining a cell phone location, using time difference of arrival technology or timing advance location measurement technology. In this embodiment, the overall communication network, perhaps at its base station, identifies the location of the device and the identified location may or may not be relayed to the terminal device. In another case, the location of the medicament device or the terminal device is determined by reference to the known location of wireless data networks that are within the range of the device. If the medicament device or terminal device or wireless carrier requires that geographic location data be obtained from the wireless network provider then the appropriate steps are taken to obtain the geographic coordinates of the medicament device or the terminal device from the network of the designated provider.

Further alternatively, the location determination may be based on a combination of both handset-based technologies and network-based technologies. Using a combination of location identification systems allows the reliable identification of the location of the medicament device and/or the terminal device, even when these devices are placed in unfavorable locations, such as within buildings or urban canyons where global positioning technologies may not function accurately or reliably, or in rural areas where network-based technologies may function unfavorably.

Accordingly, the system refers to any system that can determine the location of an object, regardless of the particular technologies used to do so and therefore is intended to encompass all such capable systems applied in various networks in various countries. For example, the system encompasses the location identification capability in the wireless Enhanced 911 standard prescribed by the United States Federal Communications Commission (the wireless E911 standard). The wireless E911 standard mandates that cellular phone service providers within the United States provide the capability to locate the position of a cellular phone making an emergency (911) call within the provider's system. The determination of location information encompasses such location identification capability as applied to all calls placed to any numbers, not limited to emergency calls nor limited to calls placed only in the United States.

Once the location and time data has been received and processed, the terminal device application formats the time and location information into a message and prepares it for transmission 311 through the wireless communication system of the cellular phone. The terminal device is connected to a network computer system via a wireless antenna 312 for two-way transfer of data between the terminal device and a network computer system 304.

The wireless communication system utilizes any one of a variety of wireless communication mediums and/or communication methods to transfer data. Examples include, but are not limited to, wireless telephony, including analog cellular, digital personal communication service (PCS), short message service (SMS), wireless application protocol (WAP), wireless metropolitan area networks (WMAN), and broadband fixed access (BWA), among others. Other suitable wireless communication mediums/methods include wireless digital data networks, such as 802.11 wireless LAN (WLAN), two-way paging networks, specialized mobile radio systems, infrared, and non-licensed ISM-service communication link, such as the BLUETOOTH protocol. Further wireless communication methods include Internet protocol (IP) addressing.

Accordingly, the wireless data communicator can be any device that communicates with the chosen wireless communication network through a wireless channel. For example, the wireless data communicator may be a cellular phone, pager, personal digital assistant, PCS handset, or personal computer. The wireless communication network may also include a network that is in part a wired network. For example, the wireless communication network may include the standard Public Switched Telephone Network (PSTN) with which the wireless data communicator interfaces.

The Internet is one suitable example of a public access network computer system, wherein the point of access thereto can be any suitable entry-point including an entry-point managed by an internet service provider. The public access network may also form part of a telecommunications system, which may itself be either a cellular system or an optical network or some other radio frequency signal network. In this embodiment, the network computer system comprises a public access network computer server system and a private access network system comprising for example, an Intranet or Ethernet which may, for example, be maintained by an individual, a commercial entity, a healthcare provider, a service provider, a pharmacy, or a university medical center. Accordingly, the terminal device can communicate with one or more third parties, such as medical centers, healthcare providers, and other suppliers of healthcare products and services via the wireless communication system and the network computer system.

Further, the medicament device and/or the terminal devices may also be arranged to communicate medication event information with other medicament devices or terminal devices in the local environment, by means of their respective communicators, facilitating patient awareness, communication, and appropriate preventive actions as warranted.

The terminal device 102 determines, based on a variety of parameters, the optimum means for transmitting information to the network computer system 304 and establishes any and all necessary connections. When a connection between the terminal device and the network computer system 304 is established, and the terminal device transmits the information about the medication event, as in the case of an event referring to dispensing of medication, the location, time and date of dispensing detected by the medication device, to the network computer system 304 in one form or another such as, but not limited to, an SMS message, an email, an http request, or some other form of data transfer.

Figure 4:
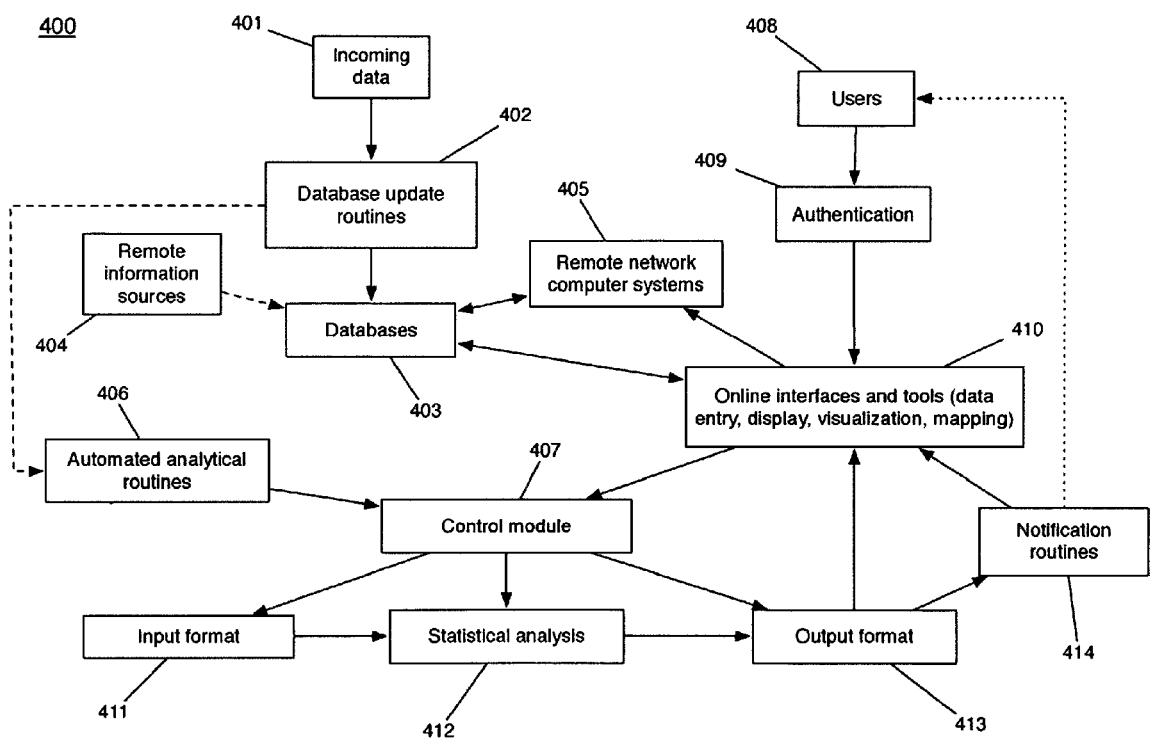
FIG. 4 is a schematic diagram outlining the software applications and the flow of information on the network computer system.

FIG. 4 is a schematic diagram outlining the software applications and the flow of information 400 on the network computer system 304. Incoming data 401 is stored in a database 403 after undergoing update routines 402. The database may also receive information from remote sources 404 and other remote network computer systems 405. Database update routines 402 are comprised of analytical routines 406 provided by the control module 407. Users 408 must be authenticated 409 to access the system using the interface tools and other user interfaces 410 provided by the system. The control module 407 executes and supervises the input format 411, statistical analysis 412 and output format 413. The input format 411 reads data from relevant databases and outputs files necessary for statistical analysis 412. Statistical analysis 412 performs analyses on files and outputs results into files. The output format 413 reformats the statistical output and saves the data to separate files to be read by applications. The output format 413 also provides notifications 414 to the user interface 410.

In another embodiment shown in FIG. 2d, the medicament device contains a means to autonomously determine its location without use of a terminal device. The means may include an built-in global positioning receiver and processor 208 and a transceiver and antenna 209 or equivalent for transmitting or receiving data, or, as described above, a network-based means or device-based technologies or a combination of both device-based technologies and network-based technologies. In this embodiment, the medicament device identifies its location autonomously as shown in FIG. 3, processes the time and date information and the geographic information, and uses its built-in wireless communication device 203 to communicate this information directly to the network computer system 304 or to the network computer system 104 via a wireless communication network 103.

The network computer server receives the medication event information triggering a variety of applications on the remote computer system or server. An initial set of applications perform a variety of functions including, but not limited, to checking the validity of the incoming data, passing the verified data to the relevant database(s), and confirming that the database(s) have been updated.

Next, applications on the server or network computer system automatically execute programs to prepare, read, analyze, and display accumulated data on medication events. A control application executes an input formatting application as necessary, which reads relevant data from the accumulated database and outputs files necessary for subsequent statistical analyses. The control program then executes a statistical analysis application as necessary, which reads the relevant files and performs statistical analysis in accordance with user established parameters, and outputs or writes the results into separate file(s). The control program then executes an output formatting application as necessary, which reformats the statistical results output files into new files to be read by applications that display the accumulated information and otherwise make the data available to authorized users.

Further, these applications select the appropriate test statistic(s) or analytical methods and process the incoming and accumulated data to identify events of interest. These events may include spatial or temporal outbreaks or clusters of medication use, or historically significant permutations from individual, geographic, clinical, epidemiologic, demographic, or spatial or temporal baselines or predicted or expected values. End users may specify, through a variety of provided tools, the scope and precise parameters of an event. When significant events are detected, the system prepares and delivers electronic notifications of the events to authorized individuals or groups, including patients themselves, some or all other patients using the system, health departments, health care providers, research teams, emergency medical providers or others. A health care provider, faced with this information, might, for example, contact the patient to initiate preventive treatment (including a change of medication, or a change of dosage) or request that the patient visit the clinic or seek emergency medical attention. Notifications provide details, for example, about the timing, location, and affected person(s) or groups involved or not involved in given event(s). In a further aspect, notifications may be distributed to an emergency assistance provider, for example a hospital accident and emergency service or an emergency help line or switchboard. The information may thus comprise a distress or emergency assist signal that requests emergency assistance.

The messages, notifications and alerts are delivered in one form or another such as, but not limited to, an SMS message, an email, an http request, a phone call, or some other form of alert.

Accompanying online interfaces and applications authorize and authenticate users. Suitably, different levels of access authorization to the network computer system will be provided to different authorized users. Examples of authorized users may include the patient, a family member or guardian, a healthcare professional such as a doctor or research professional, a database manager, a public health agency, a health insurer, a pharmacy or pharmaceutical researcher, and any combinations thereof.

Online interfaces and tools provide authorized users with the means to track the patterns and locations of medication usage over a modifiable time period through an online mapping and visualization system consisting of web-based displays, including graphic and geographic visualizations. The interfaces present a variety of tabular data and graphical visualizations and analyses of the data collected on the timing and locations of medication usage.

Further, through the interfaces provided by the network computer system, users can annotate, review, delete, update, and/or otherwise edit observations recorded by the system or otherwise provide or revise additional information such as (but not limited to) details about an event, about disease status (such as level of symptoms), perceived causes or triggers of the attacks, medical record information, health care utilization, psychological information, environmental exposure, air quality data, traffic data, pollen counts, climatic or meteorological information, or any other information relevant to disease management, clinical care, public health surveillance and practice, or scientific research.

Suitably, a variety of remote information sources may also contribute relevant data, either automatically in accordance with some pre-set algorithm, or by user instruction, to the network computer system in order to facilitate additional analyses. For example, a remote information source might be an environmental monitoring station or network of stations that automatically contributes weather, pollen counts and pollution levels, which are thereby made accessible to the system.

Further, patient accounts and medication usage data are linked to personalized instructions from their health care provider, including such information as the parameters and recommendations for when they should adjust their medication or seek medical care. The system provides means for the two-way transfer of data collected by the system, including the medicament device and the web-based system, to and from the patient's medical record(s), pharmacy record, or other electronic medical information system, such as that maintained by a health care provider, health care service, health insurer, or public health agency 405.

Further, the online interface provides a way for patients to communicate with other patients—at their discretion—in order to discuss and share information about their disease, medication use, and disease management, among other topics.

Further, the online interface offers the means for patients to provide information about the ongoing management of the disease and their experience, including, but not limited to, measurements of lung function; symptoms; health care utilization; anthropometric measurements; physiological measurements including biomarkers such as those found in exhaled breath or others to be discovered; and other types of health assessments or measures including, but not limited to, questionnaires that assess risk factors, level of asthma control, or quality of life, for example.

At the same time, interfaces and applications for authorized and authenticated physicians, health care providers, researchers and public health officials allow them to view, annotate, update, interact with, and export information about patterns of asthma medication use in individuals, and in various demographic or geographic segments. Using the web services, physicians or other authorized parties are able to monitor patients individually or in aggregate, to set parameters for notification and disease management guidance (such as compliance reminders), to establish notification thresholds, and to receive visual and statistical feedback on how well their populations or geographic areas of interest or responsibility are doing.

Accordingly, the system can deliver regular reports of usage patterns for specific demographic groups or areas, over time. In turn, the system can feed information, such as compliance information or the location or timing of medication usage, back to any remote information source 404 or remote network computer system 405 having access to the network computer system. The system can also be integrated with a healthcare management system.

The system therefore, provides the advantage of enabling data transfer with a network of computers, which can be made accessible to diverse remote information sources 404 and remote network computer systems 405, which may in turn be networked together for cross-transfer of data. The user therefore, has ready access to diverse, possibly interconnected, remote information sources capable of providing a variety of information pertaining to clinical care, disease management, epidemiological and scientific research, and public health surveillance, among other forms.

Accordingly, the present invention offers several objects and advantages. It determines the time, date, and geographic location where the medication or medical device was used. Thereby, the device allows patients, family members, health care providers, public health officials, and scientific researchers, among others, to focus on the temporal and geographic correlates (including exposures and locations) that prompt a change in the patient's condition or the use of medication.

The device provides a means to transfer information about the use of medication (location, time, date) to a network computer system either directly, or via a variety of terminal devices and/or wireless communication networks.

The device and system provides patients, family members, or health care providers with a means to monitor, evaluate and analyze patient compliance with a medication regimen over time.

The device transmits the medication event info in real-time, and, in all embodiments, does not require that the patient, health care provider or any other person participate in obtaining or transmitting the medication use information. As a result, it offers an immediate and more accurate and reliable means of assessing medication use compared to existing methods including dose logging devices, questionnaires in any form, or web-based interfaces.

Using data provided by the devices, the system can generate real-time displays and maps of asthma inhaler use for review by authorized users, including but not limited to patients, family members, health care providers or insurers, pharmaceutical companies, public health agencies, and scientific researchers, among others.

The system performs statistical analyses to automatically identify potentially important changes in the patient's immediate condition, impairment, trends over time, and future risk.

The device and system delivers information to authorized users about medication use and management that has not previously been available. This includes customizable alerts about individuals or aggregate usage.

By coordinating and aggregating data from the multitude of devices used by individuals, the device and system offers a means to conduct statistical analyses to automatically identify spatiotemporal clusters and temporal aberrations among the population (or specific geographic or demographic groups within the population) using the device.

The system combines data from medication usage patterns of individual patients to generate objective and real-time knowledge about disease in the community, a unit of analysis that has not previously been available. This includes data about the burden of disease and management practices, with respect to demographic groups or geographic areas of interest that would not be otherwise available.

The system offers aggregated information about the spatial and temporal patterns of medication use that can be used by public health and environmental health agencies to develop or evaluate surveillance activities or related clinical or public health interventions.

The device is easily adaptable to the existing variety of medication inhalers and to other medications or medical devices, including those for routine use and those for use as needed to relieve symptoms. In this way, the device can be used to monitor and indicate where and when people use or do not use preventive medications and thus allow delivery of location and time specific contextual reminders to enhance compliance, something that has never before been possible.

The device and method provides a variety of online tools to facilitate disease management by patients and their health care providers. These tools can be readily updated to incorporate the recommendations of clinical practice guidelines, and are easily adaptable to user preferences.

Other objects and advantages regarding the device and method/system include the ability to alert patients, providers and public health agencies to potentially significant events only when they occur, minimizing the time and effort required to routinely review data for important events. These alerts represent a significant improvement because they can be based on pre-set algorithms, customized parameters, ongoing statistical analysis, or some combination of these techniques.

In addition, the described device is durable and can be manufactured and sold for a low cost, representing a considerable improvement over devices described in the prior art. The described device also has low power requirements and the power supply 205 only infrequently needs to be recharged or replaced. Moreover, the device is inexpensive, rugged, and has virtually no moving parts.

Further, the device has a small size, low-profile, and discrete operation, thereby improving patient acceptance since it can be used without drawing unwanted attention to the patient or inhaler, and is more likely to be carried and used as normal, compared to devices described in the prior art which add to the size and weight of the inhaler.

The device also represents a technical improvement over devices described in the prior art that rely solely on a global positioning receiver. The device can, by means of the wireless communication network, the network computer system, or the terminal device with inherent handset-based and/or network-based location techniques, determine geographic coordinates when indoors and when in urban areas where satellite reception may be limited by buildings. Further, for the same reasons, the device and system can determine geographic coordinates in a short time period, since it can use continually-updated location information from the terminal device or the wireless communication network or the network computer system.

Further objects and advantages of the invention will become apparent from a consideration of the drawings and ensuing description.

Furthermore, other areas of art may benefit from this method and adjustments to the design are anticipated. Thus, the scope of the invention should be determined by the appended claims and their legal equivalents, rather than by the examples given.

I claim:

1. A method comprising:
    receiving, at a portable electronic device, a usage event reporting a dispensing of medication by an inhaler medicament dispensing device associated with a first user, the usage event comprising a date and a time of the dispensing of the medication;
    determining, by the portable electronic device, a geographic location of the portable electronic device in response to receiving the usage event;
    associating the geographic location with the usage event;
    transmitting, by the portable electronic device, the usage event to a remote computer system; and
    receiving, at the portable electronic device from the remote computer system, an electronic notification comprising information generated based on analysis of a plurality of accumulated usage events including the previously transmitted usage event and a usage event transmitted by a device associated with a second user, the accumulated usage events having associated timestamps and geographic locations, the analysis based on the timestamps and geographic locations associated with the accumulated usage events, the electronic notification sent responsive to the analysis performed by the remote computer system.

2. The method of claim 1, wherein the analysis comprises determining, based on the timestamps and geographic locations associated with the accumulated usage events, a potential cause of asthma symptoms, and wherein the electronic notification comprises the potential cause of asthma symptoms.

3. The method of claim 1, wherein the analysis comprises determining, based on the timestamps and geographic locations associated with the accumulated usage events, a recommended treatment strategy for a patient, wherein the electronic notification comprises the recommended treatment strategy for the patient.

4. The method of claim 1, wherein the analysis comprises generating, based on the timestamps and geographic locations associated with the accumulated usage events, a graphic visualization of timing and locations of medication usage by a patient, wherein the electronic notification provides access to the graphic visualization.

5. The method of claim 1, wherein the analysis comprises generating, based on the timestamps and geographic locations associated with the accumulated usage events, a graphic visualization of timing and locations of medication usage by a plurality of different patients, wherein the electronic notification provides access to the graphic visualization.

6. The method of claim 1, wherein the notification is generated based on parameters for when a patient should seek medical care, the parameters received from a health care provider.

7. The method of claim 1, wherein the analysis comprises generating, based on the timestamps and geographic locations associated with the accumulated usage events, a questionnaire that assesses a patient's level of asthma control or quality of life, wherein the electronic notification comprises the questionnaire.

8. The method of claim 1, wherein the analysis comprises determining, based on the timestamps and geographic locations associated with the accumulated usage events, information about a patient's compliance with a treatment regimen, wherein the electronic notification comprises the information about the patient's compliance with the treatment regimen.

9. The method of claim 1, wherein the analysis comprises:
identifying an event of interest and an event area based on the timestamps and geographic locations associated with the accumulated usage events and based on data from one or more remote information sources, the data comprising at least one from the group consisting of weather, pollen counts, and pollution levels; and
generating the notification responsive to determining that the received usage event has an associated geographic location that is within the event area, wherein the notification comprises information about the event of interest.

10. The method of claim 1, wherein the electronic notification is at least one from the group consisting of an SMS message, an email, and a HTTP request.

11. A method comprising:
receiving, at a network computer system, a plurality of usage events, the plurality of usage events including a first usage event transmitted by a first device associated with a first user and a second usage event transmitted by a second device associated with a second user, each usage event reporting a dispensing of medication by an inhaler medicament dispensing device, each of the usage events comprising a timestamp and a geographical location of the dispensing of the medication;
analyzing the usage events to identify an event of interest based on the timestamps and geographical locations of the received usage events; and
responsive to the analyzing,
preparing an electronic notification of the event of interest; and
sending the electronic notification to the first user.

12. The method of claim 11, wherein the event of interest comprises a spatial cluster of usage events.

13. The method of claim 11, wherein the event of interest comprises a temporal cluster of usage events.

14. The method of claim 11, wherein the event of interest comprises a historically significant permutation from individual, geographic, clinic, epidemiologic, demographic, or spatial baselines.

15. The method of claim 11, further comprising:
receiving from a health care provider parameters for adjusting medication; and
wherein sending the electronic notification is further based on the parameters.

16. The method of claim 11, further comprising:
receiving from a health care provider parameters for when a patient should seek medical care; and
wherein sending the electronic notification is further based on the parameters.

17. The method of claim 11, further comprising:
sending, regularly over time, a report of usage patterns.

18. The method of claim 17, wherein the report comprises at least one of demographic or geographic segments.

19. The method of claim 11, further comprising:
receiving from one or more authorized users information comprising at least one from the group consisting of:
a patient's disease status,
a perceived cause of a patient's asthma symptoms, and
a patient's medical record information; and
associating the received information regarding the patient with at least one of the usage events.

20. The method of claim 11, further comprising:
receiving from one or more authorized users or remote information sources information comprising at least one from the group consisting of:
air quality data
traffic data
pollen count data,
pollution level data, and
meteorological data; and
associating the received information with at least one of the usage events.

21. The method of claim 11, further comprising:
receiving from one or more patients information comprising at least one from the group consisting of:
measurements of lung function,
symptoms,
health care utilization,
anthropomorphic measurements,
physiological measurements, and
answers to questionnaires; and
associating the received information with at least one of the usage events.

22. The method of claim 11, wherein the electronic notification includes information regarding a timing, a location, and a list of affected persons involved or not involved in the event of interest.

23. The method of claim 11, further comprising:
creating a graphic visualization of the time and location of medication usage based on the usage events; and
wherein the electronic notification provides access to the graphic visualization.

24. The method of claim 11, wherein the electronic notification comprises a questionnaire that assesses a patient's level of asthma control or quality of life.

25. The method of claim 11, wherein the electronic notification comprises information about a patient's compliance with a treatment regimen.

26. The method of claim 11, wherein the electronic notification is at least one from the group consisting of an SMS message, an email, and a HTTP request.

\* \* \* \* \*